US008188286B2

(12) United States Patent  
Oooka et al.

(10) Patent No.: US 8,188,286 B2  
(45) Date of Patent: May 29, 2012

(54) PROCESS FOR PRODUCTION OF AZABICYCLOALKANOL DERIVATIVE

(75) Inventors: Hirohito Oooka, Takaoka (JP); Shinya Fukuhara, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 403 days.

(21) Appl. No.: 12/311,016

(22) PCT Filed: Oct. 10, 2007

(86) PCT No.: PCT/JP2007/069742
§ 371 (c)(1),
(2), (4) Date: Mar. 30, 2009

(87) PCT Pub. No.: WO2008/044702
PCT Pub. Date: Apr. 17, 2008

(65) Prior Publication Data

US 2009/0259045 A1 Oct. 15, 2009

(30) Foreign Application Priority Data

Oct. 11, 2006 (JP) .................. 2006-278150

(51) Int. Cl.
*C07D 221/02* (2006.01)
(52) U.S. Cl. ...................................................... 546/183
(58) Field of Classification Search .................... 546/183
See application file for complete search history.

(56) References Cited

OTHER PUBLICATIONS

Kim et al. Journal of Medicinal Chemistry, 2003, 46(8), 1456-1464.*
Ito et al. Tetrahedron Letters, 2003, 44, 7521-7523.*
Ito et al. Organometallics, 2001, 20, 379-381.*
Ito et al. Tetrahedron Letters, 2003 44, 7521-7523.*
Backwall, Journal of Organometallic Chemistry, 2002, 652, 105-111.*
Ito et al. Organometallics 2001, 20, 379-381.*
Kim et al., "Synthesis and Pharmacology of Site Specific Cocaine Abuse Treatment Agents: 8-Substituted Isotropane (3-Azabicyclo[3.2.1]octane) Dopamine Uptake Inhibitors," *Journal of Medicinal Chemistry*, vol. 46, No. 8, pp. 1456-1464, 2003.
Ohkuma et al., "Asymmetric Hydrogenation of 2-Arylated Cycloalkanones through Dynamic Kinetic Resolution," *SYNLETT*, No. 8, pp. 1383-1386, 2004.
House et al., "Reduction of Azabicyclic Ketones," *Journal of Organic Chemistry*, vol. 28, pp. 2407-2416, Sep. 1963.
Bäckvall, J., "Transition metal hydrides as active intermediates in hydrogen transfer reactions," *Journal of Organometallic Chemistry*, vol. 652, pp. 105-111, 2002.
Ito et al., "Rapid racemization of chiral non-racemic sec-alcohols catalyzed by $\eta(\eta^5\text{-}C_5(CH_3)_5)\text{Ru}$ complexes bearing tertiary phosphine-primary amine chelate ligands," *Tetrahedron Letters*, vol. 44, pp. 7521-7523, 2003.
De Koning et al., "Use of Achiral (Diphosphine)RuCl$_2$(Diamine) Precatalysts as a Practical Alternative to Sodium Borohydride for Ketone Reduction," *Organic Process Research & Development*, vol. 10, No. 5, pp. 1054-1058, 2006.
Supplementary European Search Report issued in Application No. 07 82 9480; Dated Jul. 26, 2010.

* cited by examiner

*Primary Examiner* — Nizal Chandrakumar
(74) *Attorney, Agent, or Firm* — Foley & Lardner LLP

(57) ABSTRACT

The object is to produce an azabicycloalkanol derivative, particularly a cis-3-substituted-3-azabicyclo[3.2.1]octan-8-ol derivative which is a useful intermediate for agricultural chemicals or pharmaceutical agents, with a good yield and at an industrially low cost. A diastereomer of an azabicyclo-$C_{6-10}$-alkanol derivative having a methyne substituted a hydroxyl group as an asymmetric carbon (e.g., a trans-3-substituted-3-azabicyclo[3.2.1]-8-ol derivative) is isomerized in the presence of a transition metal complex, thereby producing an excess amount of a thermodynamically more stable one of diastereomers (e.g., a cis-3-substituted-3-azabicyclo[3.2.1]-8-ol derivative). In this manner, a thermodynamically more stable one of diastereomers of the azabicyclo-$C_{6-10}$-alkanol derivatives can be produced.

4 Claims, 1 Drawing Sheet

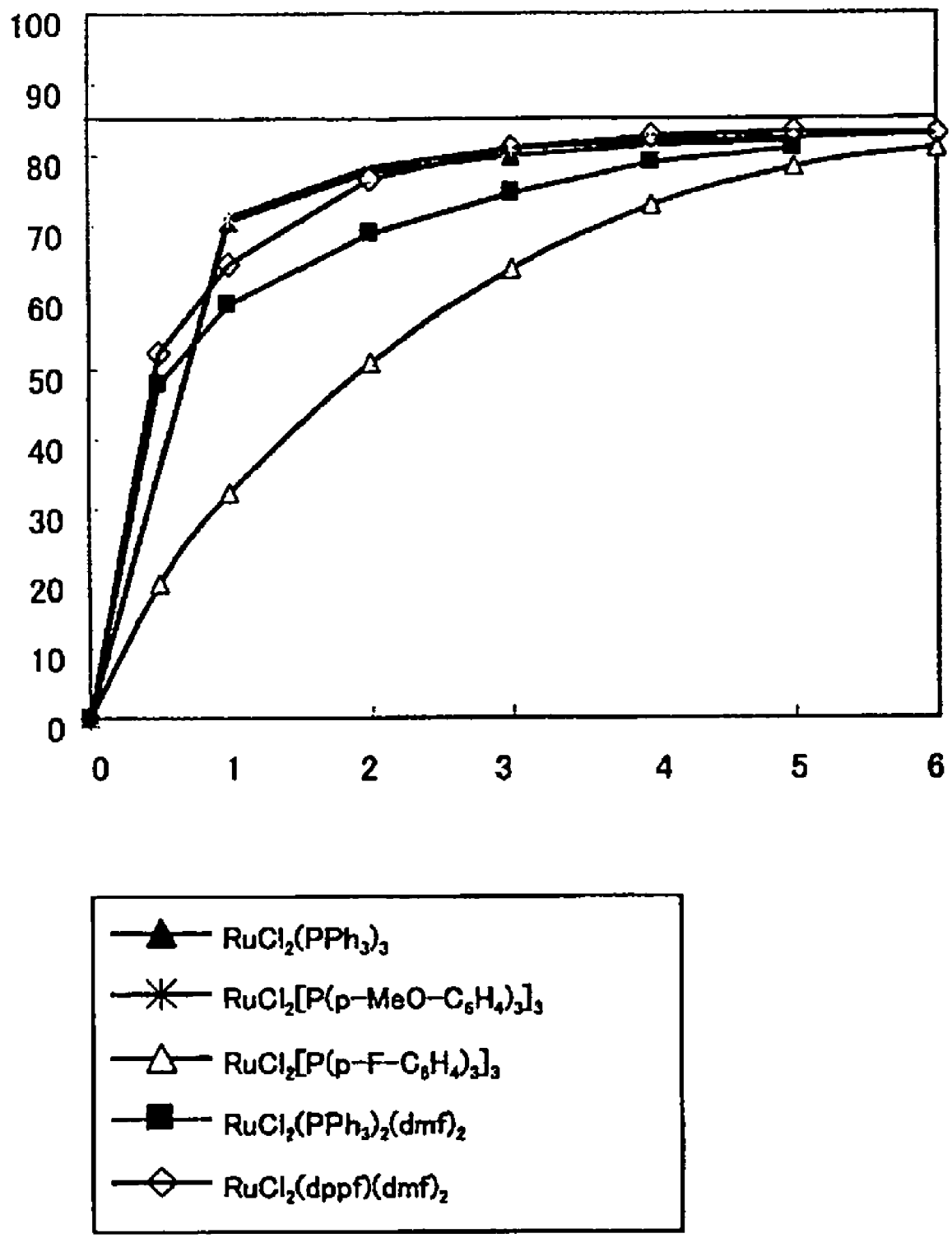

PROCESS FOR PRODUCTION OF AZABICYCLOALKANOL DERIVATIVE

TECHNICAL FIELD

The present invention relates to a novel method for producing an azabicycloalkanol derivative, particularly a novel method for producing a cis-3-substituted-3-azabicyclo[3.2.1]octan-8-ol derivative which is a useful intermediate for agricultural chemicals or pharmaceutical products. Further, in the present specification, a configuration of cis-3-substituted-3-azabicyclo[3.2.1]octan-8-ol is represented by a configuration of formula (1), and a configuration of trans-3-substituted-3-azabicyclo[3.2.1]octan-8-ol is represented by a configuration of formula (2).

BACKGROUND ART

As a method for producing a cis-3-substituted-3-azabicyclo[3.2.1]octan-8-ol derivative, for example, a method wherein 3-methyl-3-azabicyclo[3.2.1]octan-8-one is reduced with metal sodium, and heated for 230 hours in the presence of benzophenone (see Non-Patent Document 1) is known.

Further, the following method is known in which 3-methyl-3-azabicyclo[3.2.1]octan-8-one is reduced normally to obtain a trans, and transformed into triflate, and then, inversed with acid (see Non-Patent Document 2).

Meanwhile, a racemization reaction of optically active alcohol using a ruthenium complex as a catalyst is known (see Non-Patent Documents 3 and 4).

Non-Patent Reference 1: J. Org. Chem., 1963, 28, 2407
Non-Patent Reference 2: J. Med. Chem., 2003, 46, 1456
Non-Patent Reference 3: J. Organomet., Chem., 2002, 652, 105
Non-Patent Reference 4: Tetrahedron Lett., 2003, 44, 7521

DISCLOSURE OF THE INVENTION

Object to be Solved by the Present Invention

However, the method described in Non-Patent Reference 1 has problems that reaction time is long, and further, the yield of the desired cis is low. In the method of Non-Patent Reference 2, there are problems as an industrial method for producing because the reaction has to undergo many stages and anhydrous trifluoromethanesulfonate used as well as reagent is expensive. On the other hand, an example in which a reaction of a hydrogen-transfer type using a transition metal complex applied to racemization is known. However, in the case of racemization, since inversion progresses only up to 50% at a maximum, it has been considered that a preferential inversion from an isomer to another isomer is not possible.

An object of the present invention is to provide a method for producing an azabicycloalkanol derivative which is industrially useful, with a high yield and versatility. In particular, it is to provide a method for producing a cis-3-substituted-3-azabicyclo[3.2.1]octan-8-ol derivative as an azabicycloalkanol derivative.

Means to Solve the Object

The present inventors had made a keen study to solve the above mentioned objects and found out that an isomer can be preferentially isomerized from an isomer to another isomer by reacting an alcohol derivative, which is a reactive substrate, as a hydrogen source, even though the reaction is a hydrogen-transfer type using a transition metal complex.

More specifically, the first aspect of the present invention relates to a method for producing a thermodynamically more stable one of diastereomers among azabicyclo-$C_{6-10}$-alkanol derivatives, wherein a diastereomer of an azabicyclo-$C_{6-10}$-alkanol derivative containing a methyne which is an asymmetric carbon with a hydroxyl group, is isomerized in the presence of a transition metal complex, thereby producing an excess amount of the thermodynamically more stable one of diastereomers.

The second aspect of the present invention relates to a method for producing a cis-3-substituted-3-azabicyclo[3.2.1]octan-8-ol derivative, wherein a trans form in a mixture of trans- and cis-3-substituted-3-azabicyclo[3.2.1]octan-8-ol derivatives or a trans-3-substituted-3-azabicyclo[3.2.1]octan-8-ol derivative is isomerized to a cis form in the presence of a transition metal complex, thereby producing an excess amount of the cis form.

The third aspect of the present invention relates to a method for producing a cis-3-substituted-3-azabicyclo[3.2.1]octan-8-ol derivative, wherein a 3-substituted-3-azabicyclo[3.2.1]octan-8-one derivative undergoes a reduction reaction of a hydrogen-transfer type in the presence of a transition metal complex, and an organic compound with hydrogen-donating property or an inorganic compound with hydrogen-donating property to obtain a mixture of trans- and cis-3-substituted-3-azabicyclo[3.2.1]octan-8-ol derivatives or a trans-3-substituted-3-azabicyclo[3.2.1]-8-ol derivative, and then, the organic compound with hydrogen-donating property or the inorganic compound with hydrogen-donating property is removed therefrom, and the trans is isomerized to a cis form in the presence of the transition metal complex which was used for the reduction reaction of hydrogen-transfer type, and thereby producing an excess amount of the cis form.

BRIEF DESCRIPTION OF DRAWINGS

FIG. 1 is a graph showing reaction changes with the passage of time of the present invention. The vertical axis shows the ratio (%) of a cis form respect to a total of a trans form and a cis form, and the horizontal axis shows time (hr).

BEST MODE OF CARRYING OUT THE INVENTION

An azabicycloalkanol derivative used as a reactive substrate in a method for producing the present invention is a diastereomer of an azabicyclo-$C_{6-10}$-alkanol derivative having a methyne which is an asymmetric carbon with a hydroxyl group. The diastereomer is consisted of a mixture of a diastereomer containing excessively isomers of the desired diastereomer, or of only isomers of the desired diastereomer.

The azabicycloalkanol derivative used for the method for producing the present invention may have a substituent, which does not interfere an isomerization reaction using a transition metal complex, at any position on the skeleton of azabicycloalkanol.

As a substituent, the following hydrocarbon groups can be exemplified:

an aliphatic hydrocarbon group, including an alkyl group such as a methyl group, ethyl group, propyl group, isopropyl group, butyl group, isobutyl group, sec-butyl group, tert-butyl group, pentyl group, isopentyl group, and hexyl group; an alkenyl group such as a vinyl group, 1-propenyl group, 2-propenyl group, isopropenyl group, and 1-butenyl group; an alkynyl group such as an ethynyl group, 1-propynyl group, and 2-propynyl group; and a cycloalkyl group such as a cyclopropyl group, cyclobutyl group, cyclopentyl group, and cyclohexyl group.

And further, an aromatic hydrocarbon group, including a monocyclic aromatic hydrogen carbon group such as a phenyl group, o-tolyl group, m-tolyl group, and p-tolyl group; a condensed-ring aromatic hydrogen carbon group such as a 1-naphtyl group, 2-naphtyl group, and 1-anthryl group; and a ring-assembled aromatic hydrogen carbon group such as an o-biphenylyl group, and m-biphenylyl group can be exemplified.

The method for producing the mixture of trans- and cis-3-substituted-3-azabicyclo[3.2.1]octan-8-ol derivatives or the trans-3-substituted-3-azabicyclo[3.2.1]octan-8-ol derivative which is used for a reactive substrate in the method for producing the present invention is not particularly limited, and specifically, it can be obtained by reducing a 3-substituted-3-azabicylo[3.2.1]octan-8-one derivative with a normally used reagent such as $LiAlH_4$ and $NaBH_4$. Further, it may be produced by conducting a reduction reaction of hydrogen-transfer type using a transition metal complex to a 3-substituted-3-azabicyclo[3.2.1]octan-8-one derivative. In the above case, it is preferable to conduct the reaction in the presence of an organic compound with hydrogen-donating property or an inorganic compound with hydrogen-donating property. The organic compound with hydrogen-donating property or inorganic compound with hydrogen-donating property means a compound which is able to donate hydrogen by a thermal action or catalyst action. The kinds of such compounds with hydrogen-donating property are not particularly limited, but preferred examples include an alcohol compound such as methanol, ethanol, 1-propanol, 2-propanol, butanol, and benzyl alcohol, formic acid or salt thereof (e.g., ammonium salt), unsaturated hydrocarbon and a heterocyclic compound having partially a saturated carbon bond such as tetralin, hydroquinone, and phosphorous acid and the like. Among the above examples, a preferred example is an alcoholic solvent, and 2-propanol is more preferred. The usage amount of the hydrogen-donating compound to be a hydrogen source is determined by the solubility of a reaction substrate and economic efficiency, and specifically, the amount is not particularly limited, as long as it is equal to or more than the equimolar amount respect to the reaction substrate, and further a large excess amount may be used.

The mixture of trans- and cis-3-substituted-3-azabicyclo[3.2.1]octan-8-ol derivatives or the trans-3-substituted-3-azabicyclo[3.2.1]octan-8-ol derivative obtained by the reduction of hydrogen-transfer type can be used by purifying it after the reduction reaction. And the transition metal complex used herein may be used for the isomerization reaction in the next step only by removing the hydrogen-donating compound from the system which interferes the isomerization reaction. A method for removing the hydrogen-donating compound is not particularly limited, and commonly known methods such as distillation, liquid separation, and filtration can be used.

The trans-3-substituted-3-azabicyclo[3.2.1]octan-8-ol derivative may have a substituent, which does not interfere the isomerization reaction using a transition metal complex, at any position on the skeleton of 3-substituted-3-azabicyclo[3.2.1]octan-8-ol. A substituent for nitrogen at 3-position is not particularly limited, as long as the substituent does not interfere the isomerization reaction using a transition metal complex.

As a substituent, the following hydrocarbon groups can be exemplified:

an aliphatic hydrocarbon group, including an alkyl group such as a methyl group, ethyl group, propyl group, isopropyl group, butyl group, isobutyl group, sec-butyl group, tert-butyl group, pentyl group, isopentyl group, and hexyl group; an alkenyl group such as a vinyl group, 1-propenyl group, 2-propenyl group, isopropenyl group, and 1-butenyl group; an alkynyl group such as an ethynyl group, 1-propynyl group, and 2-propynyl group; and a cycloalkyl group such as a cyclopropyl group, cyclobutyl group, cyclopentyl group, and cyclohexyl group.

And further, an aromatic hydrocarbon group, including a monocyclic aromatic hydrogen carbon group such as a phenyl group, o-tolyl group, m-tolyl group, and p-tolyl group; a condensed-ring aromatic hydrogen carbon group such as a 1-naphtyl group, 2-naphtyl group, and 1-anthryl group; and a ring-assembled aromatic hydrogen carbon group such as an o-biphenylyl group, and m-biphenylyl group can be exemplified.

The Transition metal in a transition metal complex used in the method for producing the present invention is not particularly limited, as long as it is a transition metal used for Meerwein-Poundorf-Verlay reduction, or a metal capable of forming a hydride complex, and specifically, titanium, zirconium, ruthenium, rhodium, iridium, or lanthanoids can be preferably exemplified.

As a ligand of a transition metal complex, specifically, triphenylphosphine, tetraphenylcyclopentadienone, bipyridyl, thiophene, 1,5-cyclooctadiene, 1,3,5-cyclooctatriene, cyclopentadiene, pentamethylcyclopentadiene, hexamethylbenzene, diphenylphosphinylpropane, diphenylphosphinylethane, carbonmonoxide, 1,2-diaminoethane, 2-aminoethanol, 1,2-diphenylethylenediamine, cymene, and diphenylphosphinoferrocene can be exemplified.

As a transition metal complex used in the method for producing the present invention, specifically, $RuCl_2(PPh_3)_2$, $RuCl_2(PPh_3)_3$, $RuHCl(PPh_3)_2$, $RuH_2(PPh_3)_2$, $RuCl_2$-[P(p-MeO—$C_6H_4$)$_3$]$_3$, $RuCl_2$-[P(p-F—$C_6H_4$)$_3$]$_3$, $RuCl_2(PPh_3)_2$($H_2NCH_2CH_2NH_2$), $RuCl_2(PPh_3)_2$ $(dmf)_2$, $RuCl_2(dppf)(dmf)_2$, [RuCl(dppp)(Cymene)]Cl, [RuCl(biPy)(cymene)]Cl, $RuCl(PPh_3)_2(C_9H_7)$, $RuCl(PPh_3)_2(C_5H_5)$, $RhCl_2(dppp)_2$, [Ru(PPh_3)$_2$($C_9H_7$)]BF$_4$, Ru(NHCH(Ph)CH(Ph)N(Ts))(Cymene), Ru(NHCH$_2$CH$_2$O)(Cymene), $Ru_2(CO)_4(C_5(Ph)_4OH)$, $Rh_2Cl_2(biPy)_2$, $Rh_2Cl_2(dppp)_2$, $RhCl_2(thiophen)_2$, [Rh(dppp)(1,5-cyclooctadiene)]BF$_4$, [Rh(biPy)(1,5-cyclooctadiene)]BF$_4$, $Rh(PPh_3)_3Cl$, $Ir_2Cl_2(dppp)_2$, $Ir_2Cl_2(biPy)_2$, $IrCl_2(thiophen)_2$, [Ir(dppp)(1,5-cyclooctadiene)]BF$_4$, [Ir(biPy)(1,5-cyclooctadiene)]BF$_4$ can be exemplified.

Meanwhile, herein, "dppp" denotes diphenylphosphinopropane, "biPy" denotes bipyridyl, "$C_9H_9$" denotes the following formula (3), "dmf" denotes N,N-dimethylformamide, and "dppf" denotes the following formula (4).

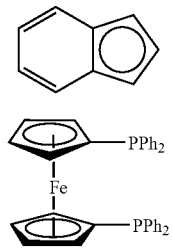

(3)

(4)

The amount of a transition metal complex used herein is not particularly limited, but a catalytic amount is preferred, and the amount is 0.005 mol % or more to a substrate to be reacted, preferably 0.02 mol % or more, and further, preferably 0.05 mol % or more.

In the method for producing the present invention, it is preferable to use a base other than the transition metal complex. The base to be used is not particularly limited, and specifically, a metal hydroxide such as sodium hydroxide, and calcium hydroxide, a metal carbonate such as potassium carbonate, metal alcoholates such as sodium ethylate, and potassium t-butoxide, organic base such as pyridine, and triethylamine, quaternary ammonium salt can be exemplified. The amount of the base to be used may be selected depending on how to generate active species and a type of hydrogen source to be used.

The isomerization reaction can be conducted by reacting a mixture of a trans form and a cis form or a trans form, which is a reactive substrate, with a transition metal complex, preferably in the presence of a base in a solvent at a temperature from room temperature to the reflux temperature of the solvent. The solvent to be used is preferably a non-hydrogen donating solvent, and specifically, an aromatic system such as toluene, benzene, xylene, and anisole, a hydrocarbon system such as hexane, heptane, and cyclohexane, an ether system such as isopropyl ether, CPME, THF, and dioxane, acetonitrile, DMF, DMSO, etc., and further, mixture solvents thereof can be exemplified.

The present invention is more specifically explained by referring to the examples hereinafter, however, the scope of the present invention is not limited to the examples.

EXAMPLE 1

1.08 g (5 mmol) of 3-benzyl-3-azabicyclo[3.2.1]octan-8-one was dissolved in 10 ml of isopropanol and 56 mg (10 mol %) of potassium t-butoxide was added, and then, nitrogen was injected into the reaction solution to deaerate oxygen. Then, 24 mg (0.5 mol %) of dichlorotris(triphenylphosphine)ruthenium was added, and the reaction solution was refluxed under a nitrogen atmosphere for 1.5 hours. After the reaction solution was cooled, 10 ml of oxygen-deaerated toluene was added and the solution was heated to distill away isopropanol, and further, heated to reflux for 8 hours. The reaction solution was immersed into water and insoluble matters were filtered, and then, the liquid was separated. Further, toluene was extracted from a water layer and organic layers are combined, and washed with saturated saline water and dried. The solvent was distilled away to obtain 1.09 g of a crude product. Recrystallization was conducted using hexane/toluene to obtain 0.65 g of the desired cis-3-benzyl-3-azabicyclo[3.2.1]octan-8-ol (cis/trans>96/4). A mixture of cis/trans≈1/1 was obtained in an amount of 0.19 g.

EXAMPLE 2

A reaction was conducted by the same process of Example 1 except the amount of a transition metal complex to be used was changed to 1 mol % and 5 mol %. The results are shown in Table 1. The reaction was observed and completed when the reaction came to equilibrium.

TABLE 1

| The amount of catalyst (mol %) | Reaction time after reduction | Cis/trans |
|---|---|---|
| 5 | 2 hours | 85/15 |
| 1 | 5 hours | 83/17 |

EXAMPLE 3

3.23 g (15 mmol) of 3-benzyl-3-azabicyclo[3.2.1]octan-8-one was dissolved in 40 ml of a mixture solvent of isopropanol/toluene (1:1), and nitrogen was injected to deaerate oxygen. 168 mg (10 mol %) of potassium t-butoxide and 28.8 mg (0.2 mol %) of dichlorotris(triphenylphosphine)ruthenium were added and the reaction solution was refluxed for 30 minutes. Isopropanol was distilled away by heating, and further, the reaction solution was refluxed for 6 hours. 12 ml of toluene was added to the reaction solution and cooled, and by filtering crystals and washing with cold toluene, 1.60 g of the desired cis-3-benzyl-3-azabicyclo[3.2.1]octan-8-ol (cis/trans>98/2) was obtained (yield 49%).

EXAMPLE 4

0.52 g (2.39 mmol) of a mixture of 3-benzyl-3-azabicyclo[3.2.1]octan-8-ol isomers (cis/trans=49/51) was dissolved in 5 ml of toluene, and nitrogen was injected to deaerate oxygen. 26.9 mg (10 mol %) of potassium t-butoxide and 2.3 mg (0.1 mol %) of dichlorotris(triphenylphosphine)ruthenium were added and refluxed for 7 hours. After the reaction solution was cooled, by adding water, extracting toluene, and concentrating the reaction solution, a crude product was obtained. Recrystallization was conducted using hexane/toluene to obtain 0.36 g of the desired cis-3-benzyl-3-azabicyclo[3.2.1]octan-8-ol (cis/trans>98/2) (yield 69%).

EXAMPLE 5

1.09 g (5 mmol) of trans-3-benzyl-3-azabicyclo[3.2.1]octan-8-ol was dissolved in 7 ml of toluene, and nitrogen was injected to deaerate oxygen. And further, the reaction solution was heated under the nitrogen flow, and after refluxing for 2 to 3 minutes, the reaction solution was cooled. 56 mg (10 mol %) of potassium t-butoxide and 0.1 mol % of any ruthenium complex were added, and heated to reflux until the reaction solution came to equilibrium. FIG. 1 shows changes with the passage of time of the reaction thereof.

INDUSTRIAL APPLICABILITY

By applying the method for producing the present invention, a thermodynamically more stable one of diastereomers of an azabicycloalkanol derivative which is a useful intermediate for agricultural chemicals or pharmaceutical products can be produced. In particular, a cis-3-substituted-3-azabicyclo[3.2.1]octan-8-ol derivative which is a useful intermediate for the agricultural chemicals or pharmaceutical products can be produced with a good yield and at an industrially low cost.

The invention claimed is:

1. A method for producing a thermodynamically more stable one of diastereomers of 3-benzyl-3-azabicyclo[3.2.1]octan-8-ol comprising, isomerizing a methyne which is an asymmetric carbon with a hydroxyl group, of a diastereomer of the 3-benzyl-3-azabicyclo[3.2.1]octan-8-ol in the presence of a ruthenium complex and a metal alcoholate, and producing an excess amount of a thermodynamically more stable one of diastereomers.

2. A method for producing cis-3-benzyl-3-azabicyclo[3.2.1]octan-8-ol comprising, isomerizing a trans form in a mixture of trans- and cis-3-benzyl-3-azabicyclo[3.2.1]octan-8-ol or trans-3-benzyl-3-azabicyclo[3.2.1]octan-8-ol to the cis form in the presence of a ruthenium complex and a metal alcoholate and producing an excess amount of the cis form.

3. The method for producing the cis-3-benzyl-3-azabicyclo[3.2.1]octan-8-ol according to claim 2, wherein the mixture of trans- and cis-3-benzyl-3-azabicyclo[3.2.1]octan-8-ol or trans-3-benzyl-3-azabicyclo[3.2.1]octan-8-ol is obtained by reducing 3-benzyl-3-azabicyclo[3.2.1]octan-8-one.

4. A method for producing cis-3-benzyl-3-azabicyclo[3.2.1]octan-8-ol comprising, conducting a reduction reaction of a hydrogen-transfer type of 3-benzyl-3-azabicyclo[3.2.1]octan-8-one in the presence of a ruthenium complex, a metal alcoholate and an organic compound with hydrogen-donating property or an inorganic compound with hydrogen-donating property to obtain a mixture of trans- and cis-3-benzyl-3-azabicyclo [3.2.1]octan-8-ol or trans-3-benzyl-3-azabicyclo[3.2.1]octan-8-ol, removing the organic compound with hydrogen-donating property or the inorganic compound with hydrogen-donating property thereof, isomerizing a trans form to a cis form in the presence of the ruthenium complex and a metal alcoholate used in the reduction reaction of the hydrogen-transfer type, and producing an excess amount of the cis form.

* * * * *